US011464835B2

(12) United States Patent
Inui (10) Patent No.: US 11,464,835 B2
(45) Date of Patent: Oct. 11, 2022

(54) ENZYME-TREATED MILK PRODUCT, PREPARATION METHOD THEREOF, COMPOSITION, AND PRODUCTS (71) Applicant: SAISEI PHARMA CO., LTD., Moriguchi (JP)

(72) Inventor: Toshio Inui, Moriguchi (JP)

(73) Assignee: SAISEI PHARMA CO., LTD., Moriguchi (JP)

( * ) Notice: Subject to any disclaimer, the term of this patent is extended or adjusted under 35 U.S.C. 154(b) by 182 days.

(21) Appl. No.: 15/578,487

(22) PCT Filed: May 31, 2016

(86) PCT No.: PCT/JP2016/066066
§ 371 (c)(1),
(2) Date: Nov. 30, 2017

(87) PCT Pub. No.: WO2016/194914
PCT Pub. Date: Dec. 8, 2016

(65) Prior Publication Data
US 2018/0133292 A1 May 17, 2018

(30) Foreign Application Priority Data

Jun. 1, 2015 (JP) .............................. JP2015-111673

(51) Int. Cl.
| *A61K 38/47* | (2006.01) |
| *A23C 21/00* | (2006.01) |
| *A61K 35/20* | (2006.01) |
| *A23L 29/275* | (2016.01) |
| *A61K 38/46* | (2006.01) |
| *A23C 9/12* | (2006.01) |
| *A23L 2/00* | (2006.01) |
| *A23L 2/38* | (2021.01) |
| *A61K 9/00* | (2006.01) |

(52) U.S. Cl.
CPC ............... *A61K 38/47* (2013.01); *A23C 9/12* (2013.01); *A23C 9/1206* (2013.01); *A23C 21/00* (2013.01); *A23L 2/00* (2013.01); *A23L 2/382* (2013.01); *A23L 29/275* (2016.08); *A61K 9/0095* (2013.01); *A61K 35/20* (2013.01); *A61K 38/46* (2013.01); *C12Y 302/01023* (2013.01); *A23V 2002/00* (2013.01)

(58) Field of Classification Search
CPC ......... A23C 21/00; A23C 9/12; A23C 9/1206; A23L 29/275; A23L 2/00; A23L 2/382; A23V 2002/00; A61K 35/20; A61K 38/46; A61K 38/47; A61K 9/0095; A61P 17/00; A61P 17/14; A61P 31/00; A61P 35/00; A61P 37/02; A61P 37/08; A61P 3/00; A61P 3/02; C12Y 302/01023
See application file for complete search history.

(56) References Cited

U.S. PATENT DOCUMENTS

| 4,091,116 A * | 5/1978 | Edwards .............. A23C 9/1206 426/42 |
| 5,177,001 A | 1/1993 | Yamamoto |
| 5,283,189 A * | 2/1994 | Takase ................... C12P 19/02 435/207 |
| 2002/0031571 A1* | 3/2002 | Couzy .................. A23C 9/1206 426/2 |
| 2003/0036638 A1 | 2/2003 | Joergensen et al. |
| 2004/0146603 A1* | 7/2004 | Dambmann ....... A23C 19/0328 426/36 |
| 2009/0098240 A1* | 4/2009 | Mills ........................ A23G 4/10 426/3 |
| 2013/0243880 A1 | 9/2013 | Uto et al. |
| 2014/0227393 A1 | 8/2014 | Chen et al. |

FOREIGN PATENT DOCUMENTS

| EP | 0020781 A1 | 1/1981 |
| EP | 2 530 148 A1 | 12/2012 |
| ES | 2183711 A1 | 3/2003 |
| GB | 1359666 A | 7/1974 |
| JP | 47-5122 A | 5/1972 |
| JP | 60-41449 A | 3/1985 |
| JP | 5-97695 A | 4/1993 |
| JP | 6-327435 A | 11/1994 |
| JP | 6-99314 B2 | 12/1994 |
| JP | 7-33673 A | 2/1995 |
| JP | 8-47381 A | 2/1996 |
| JP | 9-124473 A | 5/1997 |
| JP | 10-309178 A | 11/1998 |
| JP | 11-510620 A | 9/1999 |

(Continued)

OTHER PUBLICATIONS

Fukuda, "Transport proteins in milk," Milk Science. vol. 62, No. 2, Aug. 8, 2013, 2 pages, with English translation.
Hori et al., "Drug discovery of dramatype-anticancer drugs based on oligosaccharide-processing of Gc protein (vitamin D-binding protein)," Radiation Biology Research Communications, vol. 39, No. 3, 2004, p. 328 (3 pages provided), with English translation.
International Search Report (Form PCT/ISA/210) issued in International Application No. PCT/JP2016/066066 dated Sep. 6, 2016.
Sasaki et al., "Ushi shonyu Yurai Macrophage Ksseikazai no Sosei to Macrophage Kasseika Sayo no Kaiseki," Dai 135 Kai Abstracts of Annual Meeting of Pharmaceutical Society of Japan, 27PB-am293, Mar. 2015, 2 pages, with English translation.

*Primary Examiner* — Blaine Lankford
(74) *Attorney, Agent, or Firm* — Birch, Stewart, Kolasch & Birch, LLP (57) ABSTRACT An object of the present invention is to provide an enzyme-treated milk product, a method for preparing the same, a composition thereof comprising a pharmaceutical composition, and a product thereof comprising a pharmaceuticals. The enzyme-treated milk product can be obtained by a method for producing an enzyme-treated milk product including a step for bringing milk into contact with β-galactosidase.

9 Claims, 2 Drawing Sheets

(56) References Cited

FOREIGN PATENT DOCUMENTS

| | | |
|---|---|---|
| JP | 2000-32911 A | 2/2000 |
| JP | 2000-95697 A | 4/2000 |
| JP | 2001-46021 A | 2/2001 |
| JP | 2005-139160 A | 6/2005 |
| JP | 2014-533826 A | 12/2014 |
| WO | WO 2007/088324 A1 | 8/2007 |
| WO | WO 2008/037839 A1 | 4/2008 |
| WO | WO 2013/038997 A1 | 3/2013 |
| WO | WO 2013/072342 A1 | 5/2013 |

* cited by examiner

ENZYME-TREATED MILK PRODUCT, PREPARATION METHOD THEREOF, COMPOSITION, AND PRODUCTS

TECHNICAL FIELD

The present invention relates to an enzyme-treated milk product, a method for preparing the same, a composition thereof comprising a pharmaceutical composition, and a product thereof comprising a pharmaceuticals.

BACKGROUND ART

Macrophage has a function of treating waste products in a human body and a defensive function against pathogens such as a microbe and a virus, and tumor cells. Macrophage also has a function as an effector of cell immunity via presentation of an antigen to T cell and production of interleukin 1. Accordingly, it is important to activate macrophage for treatment and prevention of a cancer and an infectious disease, and the activation of macrophage makes it possible to carry out treatment and prevention of a cancer and an infectious disease.

A factor for activating macrophage is, for example, an interferon, and its clinical application has been carried out. In addition, it is known that a certain kind of polysaccharides has an immunostimulating activity, and some of them are expected to be developed as an antiviral agent and an anticancer agent (Patent Document 1 or 2).

Fatigue is a disease involving a variety of symptoms generally including feeling of fatigue and malaise as the main symptoms and additionally including sleep disorder, loss of motivation, and the like. Each of feeling of fatigue and malaise is one of important alarm signals that an abnormality occurs in the body, and a person are aware of such feelings even in good health, for example, when the person practices vigorous exercise or works for long hours, or when the person is in excessive stressful situations. Generally, a person recovers from such physiological fatigue to the original normal condition by rest, and thus fatigue does not last for long time. According to "the Survey on Public Attitudes toward Health" conducted by the Prime Minister's Office in 1985, a little more than approximately 60% of people complained of fatigue, but 70% of people complaining of fatigue answered that "they recovered from fatigue by overnight sleep". However, people of today often works for long hours and are in excessively stressful situations, and it is also difficult for them to take enough rest. Therefore, it is often difficult for them to recover from feeling of fatigue and malaise. An epidemiological survey conducted by the team for survey and research on fatigue, the Ministry of Health and Welfare, in 1999, reported as follows: the percentage of people having subjective fatigue was about 60%, which had not changed, but as much as 60% of them were fatigued over 6 months or more. In other words, the number of people suffering from chronic fatigue increases, and the feature of fatigue is thus changing (Non-Patent Document 1). Recently, a disease called chronic fatigue syndrome (CFS) has become a topic as an intractable disease. Patients with this syndrome exhibits basic symptoms including feeling of general fatigue, malaise, slight fever, lymph node swelling, muscle pain, joint pain, and psychoneurotic symptoms over such a long period as to hinder daily life. In addition, a death from overwork has become a big social problem. A death from overwork is defined as a sudden death due to excessive overwork over a long period of time. The problem of a death from overwork is recognized to be very important from medical, economic, and social viewpoints. Then, so-called "anti-fatigue substances" have been suggested, including substances that can attenuate fatigue that is caused when a person practices vigorous exercise or works for long hours or when a person is in excessively stressful situations, and substances that allow a person to early recover from fatigue to a normal condition. For example, it has been reported that a kind of an amino acid composition (Patent Document 3), L-carnitine- and histidine-related dipeptides (Patent Document 4), a hawthorn extract (Patent Document 5), and the like have the effects of physical strength. It also has been shown that a nutritional supplement composition including ascorbic acid is useful for the purpose of supplying nutrition at the time of, for example, physical exhaustion by exercise, etc., or fatigue (Patent Document 6).

Recently, the number of patients with diseases caused by type I allergy including hay fever, allergic rhinitis, food allergy, atopic dermatitis, and allergic asthma tends to increase worldwide. Although drug therapy using an antihistamine agent, an antiallergic agent, a steroid, or the like is generally conducted for the treatment of allergic diseases, research and development of functional foods and supplements effective for allergy as alternative healthcare has been also eagerly conducted recently from the viewpoint of preventive medicine. For example, lactic acid bacteria that act on gut immunity attract attention because it is purported that they are effective for prevention and treatment of allergic diseases (see, for example, Patent Documents 7 to 9). Gut immunity is an immune mechanism that eliminates pathogenic microorganism and the like ingested orally, and it is considered that suppression of over-response of gut immunity contributes to prevention and treatment of allergic diseases.

Alopecia refers to a condition (symptom) of hair loss due to various causes, and typical examples thereof include male pattern alopecia (baldness), seborrheic alopecia, alopecia pityroides, senile alopecia, alopecia areata, postpartum alopecia, mechanical (pressure) alopecia, and trichotillomania. Use of a substance that inhibits 5α-reductase activity to thereby suppress production of dihydrotestosterone (DHT) (Patent Document 10), for example, has been suggested for treatment of these types of alopecia, but there is a room for improvement in its effect.

Skin color of human depends on various factors including activity of melanocyte which produces melanin pigment, vascular distribution, the thickness of the skin, and presence or absence of contained pigments such as carotenoid and bilirubin. Among them, the degree of formation of melanin (black pigment), which is produced in melanocyte by enzymes such as tyrosinase, is one of the most important factors on which skin color depends. Melanin that is present in the skin has the important function of protecting the body from ultraviolet rays and the like. However, it is known that when melanin is present excessively, it not only causes skin pigmentation such as spots, freckles, and mole but also functions as a factor that accelerates skin aging to induce carcinoma cutaneum. Various substances exhibiting skin whitening effects including Kojic acid, ascorbic acid, arbutin, hydroquinone, glutathione, and derivatives thereof have been used in order to treat or attenuate skin pigmentation due to excessive production of melanin (for example, Patent Document 11), but they have various problems in terms of efficacy, safety, ease of formulation, stability, and the like. The skin is directly exposed to light and therefore is the most vulnerable part to ultraviolet rays. According to the degree of exposure, the skin exposed to ultraviolet rays shows biological response including burn injury, pigmentation, DNA damage, change in connective tissue, and cancerization. Additionally, repetitive exposure to ultraviolet rays accelerates skin aging, and such skin aging further cause formation of wrinkles, pigmentation, mutation of connective tissue, change in the thickness of epidermal cells, and the like. Connective tissue of the skin is formed mainly of collagen and elastin. Because collagen and elastin impart elasticity to the skin, the skin is easily damaged to age when they are weakened. The enzyme involved in decomposition of collagen is MMP (Matrix-Metalloproteinase). As skin aging progresses, expression of MMP increases and thus increased MMP decomposes collagen in the skin. The repetition of such a mechanism results in formation of wrinkles on the skin and early progression of aging. In order that skin tissue retains moisture, it is necessary to increase the natural-moisturing-factor in the skin. The main components of the natural-moisturing-factor are amino acids, and therefore ensuring supply thereof allows the skin to keep moisture retention.

Patent Document 12 describes that a human blood serum treated with an enzyme (β-galactosidase, or β-galactosidase and sialidase) has an activity of macrophage activation.

PRIOR ART DOCUMENT

Patent Document

Patent Document 1: JP H05-097695 A
Patent Document 2: JP H06-099314 B
Patent Document 3: JP H09-124473 A
Patent Document 4: JP 2001-046021 A
Patent Document 5: JP H08-047381 A
Patent Document 6: JP H06-327435 A
Patent Document 7: JP H10-309178 A
Patent Document 8: JP 2000-095697 A
Patent Document 9: JP 2005-139160 A
Patent Document 10: JP H07-033673 A
Patent Document 11: JP H11-510820 A
Patent Document 12: WO 2013/038997

Non-Patent Document

Non-Patent Document 1: "FATIGUE SCIENCE", pp. 222-228, Editors: Masayasu INOUE, Hirohiko KURATUNE, & Yasuyoshi WATANABE; Kodansha Co., Ltd.

SUMMARY OF THE INVENTION

Problem to be Solved by the Invention

An object of the present invention is to provide an enzyme-treated milk product which is useful for treatment, prevention, and amelioration of diseases such as a cancer and an infectious disease, a disease associated with fatigue, allergic diseases (particularly caused by type I allergy), and an alopecia, as well as improvement of skin, and a method of preparing the same. Further, the present invention provides a pharmaceutical compositions comprising the enzyme-treated milk product, pharmaceuticals and products comprising thereof.

Means to Solve the Problem

The present inventors have made intensive studies and as a result, have found that when a milk of mammalian is subjected to enzyme treatment by bringing the milk into contact with a specific enzyme, that is β-galactosidase, or β-galactosidase and sialidase, the treated milk product shows excellent activities of treatment, prevention or improvement against diseases such as a cancer and an infectious disease, a disease associated with fatigue, allergic diseases (particularly caused by type I allergy), and an alopecia, as well as improvement of skin. The present inventors have made further studies and have completed the present invention.

Namely, the present invention relates to:

[1] a method of preparing an enzyme-treated milk product comprising a step of bringing a milk into contact with β-galactosidase,

[2] the preparation method according to the above [1], further comprising a step of bringing the milk into contact with sialidase,

[3] the preparation method according to the above [1] or [2], further comprising a step of condensation, or de-cheese processing of the milk, before enzyme treating,

[4] an enzyme-treated milk product obtained by the preparation method according to any one of the above [1] to [3],

[5] the enzyme-treated milk product according to the above [4], comprising proteins in an amount of from 0.02 μg to 40 mg, preferably 0.02 μg to 20 mg, more preferably 0.2 μg to 20 mg, more preferably 2 μg to 20 mg, more preferably 20 μg to 20 mg, more preferably 200 μg to 10 mg, more preferably 200 μg to 2 mg for one dose,

[6] a pharmaceutical composition comprising the enzyme-treated milk product according to the above [4] or [5],

[7] a medicinal product comprising the pharmaceutical composition according to above [6],

[8] a composition for food or beverage, comprising the enzyme-treated milk product according to the above [4] or [5],

[9] a food or beverage comprising the composition for food or beverage according to the above [8].

Effects of the Invention

The enzyme-treated milk product of the present invention is useful for treatment, prevention, and improvement of cancer and an infectious diseases, allergy diseases (particularly, an allergy disease caused by type I allergic reactions), and alopecia, as well as improvement of skin. Therefore, the enzyme-treated milk product of the present invention can be used as a medicinal product, quasi-drug or foods or beverage for prevention, amelioration and maintenance of remission of the above-mentioned diseases.

Furthermore, the enzyme-treated milk product according to the present invention has advantages such as easy preparation and low cost since it can be prepared by treating a milk with β-galactosidase, or β-galactosidase and sialidase.

EMBODIMENT FOR CARRYING OUT THE INVENTION

<Milk>

The milk used in the present invention refers to a secretion from the mother's body of mammalian for giving babies nutrition to grow. Mammalian herein is not particularly limited and preferred example thereof include cows, horses, sheep, goats, pigs, human, buffalos, yaks, camels, donkeys, reindeer, and deer. The milk encompasses so-called colostrum, which is secreted only for a certain number of days after a delivery, but does not encompass colostrum from cows (milk secreted from a mother cow within 10 days after a delivery). The milk may be subjected to a pretreatment before enzyme treatment. Examples of the pretreatment include condensation to reduce the water content as well as removal of components (e.g. casein, fat) that solidify as cheese when making cheese from a milk (de-cheese processing). Hereinafter, a milk obtained through concentration is also referred to as a "condensed milk" and a milk obtained through de-cheese processing is also referred to as a "de-cheese ingredient milk" (whey).

<Enzyme>

Beta-galactosidase to be used in the present invention is not limited particularly, and any kind of known β-galactosidases can be used. Examples are one derived from *Escherichia coli*, one derived from bovine liver, and the like. Examples of commercially available β-galactosidases are Catalogue No. 072-04141 of Wako Pure Chemical Industries, Ltd., G1875 of SIGMA-ALDRICH, and the like.

In the present invention, β-galactosidases can be used alone or can be used in combination of two or more thereof.

Sialidase to be used in the present invention is not limited particularly, and any kind of known sialidases can be used. Examples are one derived from *Clostridium perfringens*, one derived from *Streptococcus* 6646K, one derived from *Vibrio cholerae*, one derived from *Arthrobacter ureafaciens*, and the like. Examples of commercially available sialidases are Sigma product Nos. N2876, N2133, N2904, N3001 and N5631 of SIGMA-ALDRICH, Code No. 120052 of SEIKAGAKU BIOBUSINESS CORPORATION, Catalogue #P0720L and P0720S of BioLabs, and the like.

In the present invention, sialidases can be used alone or can be used in combination of two or more thereof.

<Treatment with Enzyme>

In the present invention, it is preferable that the milk is brought into contact with β-galactosidase or sialidase (enzyme treatment) by using a sufficient amount of enzyme for a sufficient period of time to such an extent that the enzyme reaction does not proceed substantially any more. For such a purpose, though an amount and time for the treatment depend on kind of an enzyme, for example, when Catalogue No. 072-04141 of Wako Pure Chemical Industries, Ltd. is used as β-galactosidase, it is enough to use the enzyme in an amount of 65 mU to 100 μl of a milk. Further, for example, when the product No. N2876 of SIGMA-ALDRICH is used as sialidase, it is enough to use the enzyme in an amount of 65 mU to 100 μl of a milk. In this case, it is sufficient to carry out the enzyme treatment for three hours.

The enzyme treatment can be carried out in a vessel of free choice by adding these enzymes into a milk, and if desired, a buffering solution usually used in this field may be added thereto in order to adjust a total protein concentration in the milk. Examples of such a buffering solution are saline solution, phosphate buffered saline (SPB), Ringer solution, and the like.

The enzyme treatment temperature is not limited particularly as far as the enzyme exhibits its activity, and is a temperature around 37° C. where the enzyme usually shows a high activity.

The enzyme treatment is terminated by heating (heat treatment), thereby inactivating the enzyme. Such heat treatment is not limited particularly as far as the enzyme can be inactivated, and for example, can be carried out by heating at a temperature around 60° C. for about 10 minutes.

The sample after the heat treatment may be subjected to condensing if desired. The condensing can be carried out by using commercially available equipment, for example, a centrifugal thickener (for example, 10000MWCO YM-10 of MILLIPORE CORPORATION).

The enzyme treatment can be carried out also by using an enzyme fixed to a solid phase (immobilized enzyme). A method of fixing the enzyme to a solid phase is known to a person ordinarily skilled in the art, and for example, β-galactosidase and/or sialidase can be fixed to agarose beads by using a coupling agent such as cyanogen bromide. Examples of such immobilized enzyme commercially available are immobilized β-galactosidase G3M (#A3102, MoBiTec), neuraminidase agarose derived from *Clostridium perfringens* (Welch *bacillus*) (Product No. N5254 available from SIGMA-ALDRICH), and the like. An advantage of use of an immobilized enzyme is such that an enzyme can be recovered without being inactivated by heat treatment after enzyme treatment, and as a result of such recovery, contaminants (proteins such as enzyme inactivated by heat treatment, and the like) can be decreased.

<Enzyme-Treated Milk Product>

The thus obtained enzyme-treated milk product of the present invention can be formed into a solid or a powder by freeze-drying. Such an enzyme-treated milk product is a novel composition.

The enzyme-treated milk product thus obtained can be used for preparing a pharmaceutical compositions or pharmaceuticals, a composition for a quasi-drug or quasi-drug, as well as a composition for food or beverage, or food and beverage containing thereof.

<Pharmaceuticals>

The enzyme-treated milk product of the present invention can be used as a pharmaceutical composition as it is, or by optionally blending pharmaceutically acceptable auxiliaries (carriers) thereto. Any of auxiliaries used usually in this field can be used as such pharmaceutically acceptable auxiliaries, and examples thereof include a diluent, a stabilizer, a preservative, a buffer agent, an excipient, a binding agent, an antiseptic agent, a disintegrant, a lubricant, a flavoring substance and the like. These auxiliaries are blended optionally depending on a dosage form of the pharmaceutical composition.

The pharmaceutical composition of the present invention can be formed into pharmaceuticals by preparing into a proper dosage form. Such a dosage form is not limited particularly, and may be either of oral preparation or parenteral preparation. Examples of parenteral preparation include an injection agent, an infusion agent, nasal drops, ear drops, a suppository, an enteral nutrient, and the like. Examples of the injection agent include those administrated by intravenous injection, hypodermic injection, intradermal injection, intramuscular injection, intraperitoneal injection, and the like, and among these, intramuscular injection is preferred. Meanwhile, examples of the oral preparation include a powder, a granule, a tablet (including a sublingual tablet), a capsule, a pill, an enteric coating drug, a liquid for internal use (including a suspension agent, an emulsion, a syrup, and the like), an inhalant, and the like.

The dosage of the enzyme-treated milk product of the present invention varies depending on age, sex, body weight and symptom of a patient, an administration route, and the like. A representative example of the dosage for one dose is such that a total amount of proteins contained in the enzyme-treated milk product per one (1) dosage for adults is not less than about 0.02 µg, preferably not less than about 0.2 µg, more preferably not less than about 2 µg, more preferably not less than about 20 µg, more preferably not less than about 50 µg, and not more than about 40 mg, preferably not more than about 20 mg, more preferably not more than about 13 mg, more preferably not more than about 10 mg, more preferably not more than about 2 mg. The preferred dosage is, for example, within a range of from about 0.02 µg to about 40 mg, preferably from about 0.2 µg to about 40 mg, more preferably from about 2 µg to about 40 mg, more preferably from about 20 µg to about 40 mg, more preferably from about 50 µg to about 40 mg, more preferably from about 50 µg to about 40 mg, more preferably from about 50 µg to about 20 mg, more preferably from about 50 µg to about 13 mg, more preferably from about 50 µg to about 10 mg, more preferably from about 50 µg to about 2 mg. Herein, the amount of protein is calculated from a protein concentration determined based on an absorbance at a wavelength of 570 nm.

With respect to the dosing interval and the number of doses, in case of dosing the enzyme-treated milk product of the present invention with the above-mentioned dosage per one dose, the representative number of doses is 1 to 2 times per day. The dosage and the dosing interval may be optionally changed, using the total amount of proteins contained in the pharmaceutical composition as an index, as long as the total amount of proteins to be dosed is equal.

The dosage for prevention of the diseases may be the same dosage or one-half dosage in the case of the treatment or improvement of the diseases.

The enzyme-treated milk product of the present invention can be used in combination with other medicaments for prevention, treatment or improvement of the diseases. In the case of combination use, the dosage of the enzyme-treated milk product of the present invention is properly adjusted in consideration of indication, effect and dosage of the other medicaments.

<Quasi-Drug>

The enzyme-treated milk product of the present invention can be prepared as a composition for quasi-drug by blending of above-mentioned auxiliaries and the like according to necessity, and thus obtained composition for quasi-drug may be used for preparing quasi-drug contained thereof.

The composition for quasi-drug or the quasi-drug can be formed into a solution, a suspension, a syrup, a granule, a cream, a paste, a jelly, and the like, and can be formed into a desired shape if necessary.

The preparation of the composition for quasi-drug or a quasi-drug can be carried out by usual method.

The amount of the enzyme-treated milk product of the present invention when used as a composition of quasi-drug, or a quasi-drug is not limited particularly, and can be set optionally by referring to the dosage in the case of the above-mentioned pharmaceuticals.

<Food or Beverage>

The enzyme-treated milk product of the present invention can be formed into a composition for food and beverage by optionally blending thereto the above-mentioned auxiliaries and various kinds of additives such as a sweetener, a spice, a seasoning, an antiseptic agent, a preservative, a sanitizer, and an anti-oxidant which are usually used for a food or beverage, and also can be formed into a food or beverage comprising the composition for food or beverage by further processing the composition. The composition for food or beverage or the food or beverage can be formed into various shapes such as a solution, a suspension, a syrup, a granule, a cream, a paste, a jelly, and the like, and can be formed into a desired shape if necessary. Furthermore, the food or beverage can be formed into various shapes such as bread, noodle, confectionary, beverage, soup and fabricated food. Preparation of the composition for food or beverage and the food or beverage can be carried out by usual method.

The amount of the enzyme-treated milk product of the present invention when used as a composition for food or beverage, or a food or beverage is not limited particularly, and can be set the same dosage or optionally by referring to the dosage in the case of the above-mentioned pharmaceuticals.

The food or beverage of the present invention can be an orally ingestible so-called health foods, health beverages, functional foods, nutrition function foods, dietary supplements, nutritional supplementary foods (supplements), foods for special dietary uses, foods for specified health uses, and feeding stuff for animals other than a human being, such as work animals, hound dogs, racehorse, pet animals, and the like.

The pharmaceuticals, quasi-drugs, and food or beverage of the present invention as mentioned above are preferably in such a form allowing the enzyme-treated milk product being an active ingredient to be absorbed via a digestive tract, preferably via an oral cavity or an intestine (for example, in a form of a sublingual tablet or an enteric coating drug as mentioned above).

<Apply Symptoms>

(Cancers, Infectious Diseases)

Cancers include any of carcinomas, sarcomas and malignant tumors, for example, carcinoma cutaneum, bronchial carcinoma, lung cancer, non-small-cell lung cancer, mammary cancer, ovarium cancer, tongue cancer, pharyngeal cancer, esophageal carcinoma, gastric cancer, intestinum tenue cancer, intestinum crassum cancer, rectum cancer, colon cancer, hepatic cancer, pancreas cancer, renal cancer, renal cell carcinoma, vesical cancer, prostatic cancer, uterine cancer, cervical cancer, Wilms' tumor, melanotic carcinoma, meningioma, neuroblastoma, osteosarcoma, Kaposi sarcoma, lymphoma, leukemia, and the like. In addition, herein, the term "cancer" includes these malignant tumors and metastases thereof.

Further, examples of infectious diseases are viral infectious diseases and bacterial infectious diseases, and for example, there are exemplified HIV infectious diseases, AIDS, and in addition, hepatitis b, hepatitis c, herpes, influenza, pneumonia, tuberculosis, EB virus infection, and the like.

The pharmaceutical composition of the present invention has a macrophage activating action, and therefore, can be used as a therapeutic agent or a prophylactic agent for diseases such as cancers and infectious diseases.

(Fatigue)

Fatigue refers to a condition developed as a temporary lowering of physical and/or mental performance when physical or mental burden is continuously given. A lowering of performance herein means a qualitative or quantitative lowering of physical and/or mental working capacity. The term "fatigue" of the present invention also encompasses chronic fatigue as well as fatigue from chronic fatigue syndrome and fatigue leading to a death from overwork.

"Effects of improving or treating fatigue" in the present invention refers to the effect of attenuating fatigue and the effect of recovery from fatigue described above, and specifically refers to prolongation of the duration of activity of a site of exercise or action (including the brain); suppression of increase in fatigue substances compared to that due to the same amount of exercise or activity (improvement in physical endurance and enhancement in physical strength); improvement of the condition where the brain, the nerve, and the like sense fatigue though the site of exercise or action is not fatigued; and the effect of accelerating recovery of the site of exercise or action from a fatigue condition to a normal condition. "Preventive effect on fatigue" in the present invention refers to the effect of inhibiting getting to be in the fatigue condition aforementioned.

Chronic fatigue syndrome, the definition of which is not established definitely, refers to a syndrome featuring continuous weakness or fatigue at such a level as to hinder daily life and the syndrome involves nonspecific physical symptoms lasting over six months or more and is not caused by other factors (Stedman's Medical Dictionary, sixth revised edition).

A death from overwork refers to the following condition: although a person is in too sever overwork conditions to keep physical vitality, the person cannot feel fatigue enough, and as a result, the person develops a cerebral vascular disease or a heart disease to thereby result in permanent disablement from laboring or death.

The enzyme-treated milk product according to the present invention can treat such chronic fatigue syndrome, specifically, can alleviate various symptoms of chronic fatigue syndrome to thereby bring a subject to a normal condition, and also can prevent a death from overwork.

(Allergic Diseases)

Allergic diseases herein refer to allergic diseases caused by at least type I allergy, and type I allergy herein is defined by Coombs classification. Therefore, examples of "allergic diseases caused by at least type I allergy" include hay fever, allergic rhinitis, bronchial asthma, urticaria, atopic dermatitis, food allergy, eosinophilic pneumonia, food allergy, and anaphylactic shock. Among them, hay fever and atopic dermatitis are preferable.

The enzyme-treated product according to the present invention can treat, prevent, or improve these allergic diseases.

(Alopecia)

Alopecia refers to the condition (symptom) of hair loss due to various causes. Typical examples thereof include male pattern alopecia (baldness), seborrheic alopecia, alopecia pityroides, senile alopecia, alopecia areata, postpartum alopecia, mechanical (pressure) alopecia, and trichotillomania (mental disease). Among them, alopecia areata is preferable.

The enzyme-treated milk product according to the present invention exhibits an excellent effect of promoting hair restoration and hair growth, and therefore can prevent, treat, or improve alopecia.

(Improvement of Skin)

Improvement of skin refers to skin whitening, suppression or improvement of pigmentation (e.g., spots, freckles, dullness of skin, senile pigment spot, mole, nevi, and dark circle), promotion of keratin removal or keratin turn-over, anti-aging, suppression or improvement of wrinkles, moisturization, or regeneration. Among them, skin whitening, suppression or improvement of pigmentation, and suppression or improvement of wrinkles are preferable.

The enzyme-treated milk product according to the present invention exhibits an effect in improvement of skin above described.

Example

The present invention is explained in detail by means of Examples, but is not limited to those examples.

1. Preparation of Enzyme-Treated Milk Product (1)

1 mg of solid bovine milk was dissolved in 1 ml of 1×PBS, and to 100 µl of this solution were added 6.5 µl of β-galactosidase (10 mU/µl, Catalog No. 072-04141 available from Wako Pure Chemical Industries, Ltd.), 6.5 µl of sialidase (10 mU/µl, N2876 available from SIGMA-ALDRICH) and 87 µl of 100 mM SPB (15.601 g of $NaH_2PO_4.2H_2O$ and 35.814 g of $Na_2HPO_4.12H_2O$ were dissolved in 500 ml of distilled water to prepare 200 mM SPB (pH 7.0), followed by dilution into 100 mM SPB), followed by 3-hour incubation at 37° C. After the incubation, 200 µl of 100 mM SPB was further added thereto, followed by 10-minute heat treatment at 60° C. After the heat treatment, the solution was condensed with a MICROCON (10000MWCO YM-10, MILLIPORE CORPORATION), and a protein concentration was determined based on an absorbance at a wavelength of 570 nm (using a calibration curve made with respect to BSA (bovine serum albumin, SIGMA, A4503)). Thereby the protein concentration (µg/µl) of the solution was determined. (Sample 1).

Sample 1 was diluted using 100 mM SPB to prepare samples, each having protein concentrations of 1 ng/10 µl (Sample 1-1), 10 ng/10 µl (Sample 1-2), and 100 ng/10 µl (Sample 1-3), respectively.

Meanwhile, a protein concentration of the milk before the enzyme treatment (Comparative Sample 1) was determined in the same manner as above. Comparative Sample 1 was diluted using 100 mM SPB to prepare samples, each having protein concentrations of 1 ng/10 µl (Comparative Sample 1-1), 10 ng/10 µl (Comparative Sample 1-2), and 100 ng/10 µl (Comparative Sample 1-3), respectively.

<Phagocytotic Activity of Macrophage (1)> (Phagocytotic Activity of Intra-Abdominal Mouse Macrophage by Using Opsonized SRBC.)

A mouse (ICR female mouse) was made to suffer from cervical dislocation, an integument of its abdomen was peeled off, and 10 ml of phosphate buffered saline (PBS containing 0.01 M of sodium phosphate, 0.9% NaCl and 5 units/ml of heparin) was injected in its abdominal cavity without injuring viscera. After tapping of the abdomen for about one minute, an intra-abdominal liquid was recovered to collect peritoneal cells. After subjecting the recovered intra-abdominal liquid to centrifuging (1500 rpm, 4° C., 15 minutes), a supernatant was disposed, and an RPMI culture medium was added, followed by pipetting. The number of cells was measured with a Burker-Turk hemacytometer, and an RPMI culture medium was further added to adjust the number of cells to be $1.0 \times 10^6$ cells/ml. The RPMI culture medium was prepared in such a manner as mentioned below. Namely, after dissolving a powder culture medium (Catalogue No. 856846 available from GIBCO) in 900 ml of purified water, further, 2 g of $NaHCO_3$ was dissolved thereinto in a clean bench. After adjusting a pH value of the mixture to be 7.2 with 1N HCl, the total amount of the mixture was adjusted to be 1000 ml with purified water. The thus obtained solution was subjected to filtering with a filter (SLGVJ13SL of MILLIPORE) to obtain an RPMI culture medium which was then stored at 4° C. before the use.

The macrophage solution obtained above was dispensed in each of wells on a plate with 24 wells (TPP, 92024) in an amount of 500 μl/well ($5.0 \times 10^5$ cells/well), in which three sterilized cover glasses (Micro cover glass No. 1 of Matsunami Glass Ind., Ltd.) were put in each of wells. Further, an RPMI culture medium was added in an amount of 500 μl/well to be totally 1 ml/well. After subjecting the plate to 1-hour incubation at 37° C., the solutions in each of the wells were disposed, and each well was washed with 1 ml of RPMI culture medium twice. After the washing, 1 ml of an RPMI culture medium was added in each of wells, followed by 15-hour incubation at 37° C.

After the incubation, 10 μl each of Samples 1-1 to 1-3 and Comparative Samples 1-1 to 1-3 prepared above was added in each well, followed by 3-hour incubation at 37° C. to stimulate the macrophages. After the incubation, the solutions of each well were disposed, and 1 ml of 0.5% opsonized SRBC (sheep red blood cells of Nippon Bio-Supp. Center) was added, followed by 90-minute incubation at 37° C. to make the macrophages phagocytose the SRBC. After the phagocytosis, the cover glasses were washed with ⅕×PBS, 1×PBS and 1×PBS in order, followed by air drying for about 30 minutes. After the air drying, each cover glass was dipped in methanol (25183-2B of KANTO CHEMICAL CO., INC.) for about one minute to fix methanol to the cover glass. After the fixing, the cover glass was subjected to about 30-minute air drying again and then staining with a Giemsa solution (A1327 of SIGMA) diluted 20 times with PBS was conducted for one hour. After the staining, the cover glass was washed with tap water from its back surface and air-dried overnight.

Figure 1:
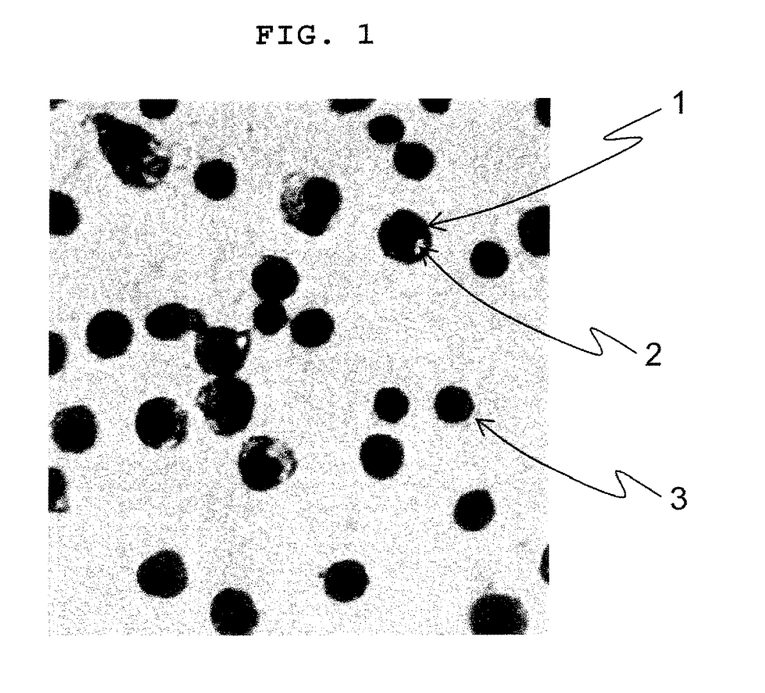
FIG. 1 is a photograph used in place of a drawing, which shows the state of macrophages subjected to Giemsa-staining.

After the air drying, the back surface of the cover glass was stuck to a slide glass (micro slide glass 52215 of Matsunami Glass Ind., Ltd.). Photographs were taken at 9 points per one cover glass with a light microscope (ECLIPSE E200 of Nikon Corporation). The number of macrophages, the number of phagocytosed SRBCs and the number of phagocytosing macrophages which were observed totally were counted and the respective total numbers at 9 points were summed up. An ingestion index was calculated by multiplying a ratio of macrophages having phagocytosed SBRC to the total macrophages counted by an average number of ingestions of one macrophage. For reference, FIG. 1 is a photograph after the Giemsa staining, which shows the states of "phagocytosing macrophages" and "phagocytosed SRBCs". By the Giemsa staining, macrophages are observed as purple spheres and SRBCs are observed as transparent spheres. The ingestion index was calculated based on the condition that SRBCs being in contact with macrophages were deemed as phagocytosed SRBCs and macrophages being in contact with SRBCs were deemed as phagocytosing macrophages.

For each of samples, two or three ingestion indices were calculated in the respective cover glasses, and an average thereof was obtained. With respect to a control, operations therefor were carried out in the same manner as above using RPMI culture media instead of the samples or comparative samples.

(Results)

Each Samples show the excellent ingestion indices in comparison with those of Control and the Comparative Samples.

<Phagocytotic Activity of Intestinal Macrophages>
(Preparation of Each Samples)

A milk sample was prepared by diluting the un-treated bovine milk to 100 μg/ml with 100 mM PBS (pH=7.0).

An enzyme-treated milk product sample was prepared by diluting the enzyme-treated bovine milk product to 100 μg/ml with 100 mM PBS (pH=7.0).

(Preparation of Medium)

To 17 ml of an RPMI culture were dissolved 2 ml of collagenase D (Roche, 11088858001) and 1 ml of DNase I (Roche 11284932001), followed by heating at 37° C. to prepare a collagenase medium.

(Measurement of Phagocytotic Activity)

In an abdominal cavity of a C57BL/6 female mouse (7-week old) was administrated 400 μl of chloral hydrate (Sigma, A2374) for anesthetization. A right abdomen of the mouse was dissected to expose the bowel, and after administration of each sample (1 mg/kg), the abdomen was closed. One hour after the administration, the abdomen was dissected again to expose the bowel, a non-tagged OVA protein (SIGMA, A5503-1G) and AF488 tagged OVA protein (Life Technologies, 034781) were administrated, and the abdomen was closed. One hour after the administration, the mouse was made to suffer from cervical dislocation, and the bowel was taken out. Fat and a Payer's patch were removed and cleaned with PBS while being careful in order not to injure the taken-out bowel. The bowel was cut into about 2 cm and was poured into 50 ml of an FACS buffer solution (prepared by adding 5 ml of FBS (inactivated) (available from GIBCO, 10437), 1 ml of EDTA (available from Nacalai Tesque, Inc., 15111-45, 500 mM), 1 ml of HEPES (available from MP, 1688449, 1M), 500 μl of sodium pyruvate (available from GIMCO, 11360-070, 100 mM), 20 μl of polymyxin B sulfate (available from GIMCO, 21850-029, 25 mg/ml) and 500 μl of penicillin/streptomycin (available from GIMCO, 15140-122, 10,000 U/ml) into 41.98 ml of phosphate buffered saline (PBS containing 0.01 M of sodium phosphate, 0.9% NaCl and 5 units/ml of heparin)) heated to 37° C., followed by 20-minute stirring (about 250 rpm) with a stirrer in an incubator at 37° C.

After the stirring, the bowel was taken out and washed three times with 30 ml of PBS. The bowel was placed on a dish of 10 cm diameter having a 10% FBS/RPMI culture. 4 ml of a collagenase medium was put in the dish, and the bowel was cut. In addition, 11 ml of a collagenase medium was put in the dish, and the dish was allowed to stand. Floating bubbles and fats were removed with an aspirator. The tissue in a vial was transferred into a flask. After the vial was washed with 5 ml of a collagenase medium, the washing liquid was put in the flask. The flask was put in a 37° C. incubator, and the content was subjected to one-hour stirring. After the stirring, 400 μl of 0.5 M EDTA (obtained from PBS having a pH of 8.0) was added thereto, followed by further 5-minute stirring. After the stirring, a supernatant was transferred to a tube capped with a cell strainer (FALCON, 352360). Meanwhile, 10 ml of the FACS buffer solution heated to 37° C. was added to the tissue, and was subjected to suspension. The whole suspension was passed through the cell strainer and debris remaining on the top of the strainer was squeezed out. The suspension was subjected to 10-minute centrifuging at 20° C. at 1,800 rpm. After the centrifuging, the supernatant was removed and the tissue was dispersed. The tissue was subjected to suspension with 10 ml of a 40% percoll, and the suspension was transferred to the tube and 5 ml of 75% percoll was put into the bottom of the tube with a capillary, followed by 20-minute centrifuging of the tube at 20° C. at 2,000 rpm. After the centrifuging, about 7 ml of the 40% percoll was removed with an aspirator from the top of the tube. After the removal, about 6 ml of the FACS buffer solution was added to the tube containing 5 ml of the FACS buffer solution, and further the 40% percoll was added thereto so that the total amount of the FACS buffer solution became 14 ml, followed by 10-minute centrifuging of the tube at 20° C. at 1,800 rpm. After the centrifuging, the supernatant was removed and 2 ml of the FACS buffer solution was put into the tube for suspension, and 1 ml of the solution was transferred to another tube, followed by 3-minute centrifuging of the tube at 20° C. at 1,500 rpm.

After the centrifuging, the supernatant was removed and 2 ml of the FACS buffer solution was added into the tube, and then Pacific® anti-mouse F4/80 antibody (Biolegend, 123124), PE/cy7 anti-mouse/human CD11b antibody (Biolegend, 101216) and CD16/32 anti-body (BD, 553141) were added thereto, followed by reaction at 4° C. Fifteen minutes after, the supernatant was removed and 2 ml of a wash buffer was added thereto, followed by 3-minute centrifuging at 20° C. at 1,500 rpm. After the centrifuging, 200 µl of a solution of 1 µg/ml 7-aminoactinomycin D (Sigma, A9400) was added thereto, and phagocytotic activity of intestinal macrophages was determined.
(Results)

In the enzyme-treated milk product, phagocytotic activity of ovalbumin (OVA) positive macrophage in an intestine was increased more as compared with a non-enzyme-treated milk.

2. Preparation of Enzyme-Treated Milk Product (2)

Each of samples having protein concentrations of 10 ng/10 µl (Sample 2-1) and 100 ng/10 µl (Sample 2-2), respectively was prepared by treating in the same manner as in the "Preparation of Enzyme-Treated Milk Product (1)" except that sialidase was not used.
<Phagocytotic Activity of Macrophage (2)> (Phagocytotic Activity of Intra-Abdominal Mouse Macrophage by Using Opsonized SRBC.)

Ingestion indices were obtained in the same manner as in "Phagocytotic Activity of Macrophages (1)" using the above samples, and as the results, each Samples show the excellent ingestion indices in comparison with that of Control.

3. Preparation of Enzyme-Treated Milk Product (3)

1 g of bovine milk (solid) is dissolved in 100 ml of 50 mM SPB (15.601 g of $NaH_2PO_4.2H_2O$ and 35.814 g of $Na_2HPO_4.12H_2O$ were dissolved in 500 ml of distilled water to prepare 200 mM SPB (pH 7.0), followed by dilution into 50 mM SPB) by stirring to prepare a 1% solution. The solution is subjected to centrifuging at 8000 rpm and 4° C. for 1 hour. The supernatant is subjected to filtration through a G2 membrane and membranes of 8 µm, 5 µm, 1.2 µm, and 0.2 µm (MILLIPORE, nitrocellulose filters) in this order. The filtrate is subjected to dialysis through a hollow fiber membrane (Asahi Kasei Chemicals Corporation, pencil type module SEP-0013).

β-Galactosidase (Catalog No. 072-04141 available from Wako Pure Chemical Industries, Ltd.) immobilized with a formyl resin (TOYOPEARL, AF-Formy-650M) is added thereto in an amount of 1 U per milligram of milk, followed by 1-hour incubation at 37° C. After incubation, the reaction solution is filtered through a G2 membrane to remove the immobilized enzyme in the reaction solution. The filtrate is subjected to filtration through a 0.2 µm filter. The protein concentration of the filtrate after filtration is determined based on an absorbance at a wavelength of 570 nm (using a calibration curve made with respect to BSA (bovine serum albumin, SIGMA, A4503)). Thereby the amount of protein recovered from 1 g of milk is determined.

The filtrate after filtration above is rapidly frozen using cold methanol and then left to stand at −80° C. to freeze completely. The resultant is dried in vacuo to powderize to thereby obtain enzyme-treated milk product (3). A part thereof is reconstituted, and the protein concentration of the resultant is determined based on an absorbance at a wavelength of 570 nm (using a calibration curve made with respect to BSA (bovine serum albumin, SIGMA, A4503)). Thereby the amount of protein from 1 g of milk is determined.

An enteric capsule in which the amount of protein contained was adjusted to 1.0 mg was prepared by using enzyme-treated milk product (3) according to a usual method. The enteric capsule was administered to a subject twice a day, specifically, morning and evening.
(Chronic Fatigue Syndrome)

When the capsule is administered to a patient with chronic fatigue syndrome for five months, feeling of fatigue and loss of motivation highly improve.
(Allergic Diseases Caused by at Least Type I Allergy)

When the capsule is administered to a patient with atopic dermatitis for three months, the condition of the skin becomes calm, and swelling, redness, and itching subside, thereby resulting in the soft and smooth skin. When the capsule is administered to a patient with hay fever for one month, itching of the eyes improves and symptoms such as nasal mucus and sneeze disappear.
(Alopecia)

When the capsule is administered to a patient with alopecia areata for one month, new hairs come out.
(Spots, Freckles, or Wrinkles)

When the capsule is administered to a patient having spots, freckles, or wrinkles, spots and freckles become faint and the skin becomes smooth. Also, the texture of the skin becomes fine.

4. Preparation of Enzyme-Treated Milk Product (4)

A crude de-cheese ingredient milk obtained through de-cheese processing (whey available from Zao dairy center) was subjected to centrifuging at 8000 rpm and 4° C. for 1 hour, and the supernatant was recovered with care about the precipitate. Distilled water (Mill-Q grade; hereinafter distilled water of the same grade was used unless otherwise noticed) in the same amount as that of the supernatant recovered was added thereto, and the resultant was subjected to dialysis through a pencil type module UF membrane (Funakoshi Co., Ltd., AIP-0013D). At this time, dialysis was continued until the amount of filtrate reached the amount equal to that of distilled water added, thereby obtaining a de-cheese ingredient milk (whey). The protein concentration was determined based on an absorbance at a wavelength of 570 nm (using a calibration curve made with respect to BSA (bovine serum albumin, SIGMA, A4503)).

The de-cheese ingredient milk obtained above was dispensed so that the amount of the protein is 6 g, and β-galactosidase (available from Oriental Yeast Co., ltd.; derived from E. coli) immobilized with a formyl resin (TOYOPEARL, Formy-650M) was added to the de-cheese ingredient milk in an amount of 4 g/6000 U, followed by 1-hour incubation at 37° C. After incubation, the reaction solution was filtered through a glass filter to separate the formyl resin. The formyl resin was washed with distilled water and stored for repetitive use. The filtrate was filter-sterilized with LABO DISC (Advantec Toyo Kaisha, Ltd.; 50CP020AS). The filtrate sterilized was lyophilized to powderize to thereby obtain enzyme-treated milk product (4) in the form of a preservable powder.

<Phagocytotic Activity of Macrophage (3)> (Phagocytotic Activity of Intra-Abdominal Mouse Macrophage by Using Opsonized SRBC.)

Each of samples having protein concentrations of 10 ng/10 μl (Sample 4-1) and 100 ng/10 μl (Sample 4-2), respectively was prepared by using the powdery enzyme-treated milk product obtained above. Each comparative samples having protein concentrations of 10 ng/10 μl (Comparative Sample 4-1) and 100 ng/10 μl (Comparative Sample 4-2), respectively was prepared from the de-cheese ingredient milk before the enzyme treatment, by diluting with 100 mM PBS, if necessary.

Further, a sample having LPS (Lipopolysaccharide, from *Escherichia coli*, SIGMA, L2755) of 1 μg/10 μl was prepared as a positive control.

Protein concentration was determined based on an absorbance at a wavelength of 570 nm (using a calibration curve made with respect to BSA (bovine serum albumin, SIGMA, A4503)).

Ingestion indices were obtained in the same manner as in "Phagocytotic Activity of Macrophages (1)" using the above samples (n=3). The results are shown in Table 1 below.

The enzyme-treated milk product more increased the phagocytotic activity of intra-abdominal mouse macrophage in comparison with un-treated milk.

TABLE 1

| | Amount of protein (ng) | Ingestion index (average value) |
|---|---|---|
| Control | 0 | 13.43 |
| Positive Control (LPS) | 1000 | 21.63 |
| Comparative Sample 4-1 | 10 | 14.85 |
| Sample 4-1 | 10 | 17.59 |
| Comparative Sample 4-2 | 100 | 15.03 |
| Sample 4-2 | 100 | 19.62 |

5. Western Blotting (1) for the Enzyme-Treated Milk Product (4) and the De-Cheese Ingredient Milk. (Using WAF as Primary Antibody)
(Preparation of Sample)

WIDE-VIEW™ Prestained Protein Size Marker III (available from Wako Pure Chemical Industries, Ltd., 230-02461) was used as Marker.

A de-cheese ingredient milk diluted to 1 mg/ml with 100 mM PBS (pH=7.0) was used as a de-cheese ingredient milk.

An enzyme-treated milk product diluted to 1 mg/ml with 100 mM PBS (pH=7.0) was used as an enzyme-treated milk product.

Each of the above samples was diluted to 1 μg/μl with distilled water, and 5 μl of each sample was mixed with 5 μl of a sample buffer (prepared by adding 50 μl of 2-mercaptoethanol (available from SIGMA, A2029) to 950 μl of Laemmli Sample Buffer (available from BIO-RAD, 161-0737), followed by 10-minute heat treatment at 100° C. to obtain a sample for electrophoresis.

An electrophoresis gel (XV PANTERA GEL, DRC, NXV-381D20) was set on an electrophoresis chamber (ERICA-MP, DRC, XVE-0MPC), and the electrophoresis chamber was filled with an electrophoresis buffer (prepared by dissolving a high speed SDS-PAGE electrophoresis buffer (available from DRC, NXV-BUFPTG) with 1,000 ml of distilled water). Each of the samples for electrophoresis was applied to each well of the set gels, followed by electrophoresis at 300 V. Amounts of samples applied for electrophoresis were 5 μl at a lane 1, 5 μl at lanes 2, and 5 μl at lane 3. After completion of the electrophoresis, the top portion of the gel was cut and disposed, and the gel was set on a transfer device (MINICA-MP, DRC, XVE-0MPB). A PVDF film (BIO-RAD, 162-0177) dipped for one minute in methanol (Kanto Chemical Industry Co., Ltd., 25183-2B) was placed on the gel, and transferring was carried out at 47 V for 30 minutes.

After the transferring, the film was washed three times for 10 minutes with TBS-T (prepared by dissolving 8.0 g of NaCl, 0.2 g of KCL and 3.0 g of $H_2NC(CH_2OH)_3$ with 1,000 ml of distilled water to adjust a pH value to 7.4 and adding thereto 1 ml of polyoxyethylene (20) sorbitan monolaurate (available from Wako Pure Chemical Industries, Ltd., 167-11515)). The film was dipped in a blocking solution (prepared by dissolving 100 mg of BSA (bovine serum albumin, SIGMA, A4503) with 10 ml of TBS-T), followed by one-hour shaking at room temperature. The film was washed three times for 10 minutes with TBS-T and dipped in a primary antibody WFA (5 μl) [prepared from 2 mg of WFA Lectin (*Wisteria floribunda* Lectin, biotin conjugate, lyophilized powder, available from Funakoshi Co., Ltd., B-1355) diluted with 1 ml of 100 mM SPB (pH=7.0)) diluting with 10 ml of TBS-T], followed by one-hour shaking at room temperature. The film was washed three times for 10 minutes with TBS-T and was dipped in secondary antibody streptavidin (prepared by diluting 2 μl of streptavidin (available from GE Healthcare, RPN-1231) with 10 ml of TBS-T), followed by one-hour shaking at room temperature. The film was washed three times for 10 minutes with TBS-T.

The film was subjected to reaction with an ECL solution (prepared by adding 1 ml of a detection reagent 2 (ECL Western Blotting Detection Reagent, available from GE Healthcare, RPN2106V2) to 1 ml of a detection reagent 1 (ECL Western Blotting Detection Reagent, available from GE Healthcare, RPN2106V1)) for one minute in a plastic vessel, and pictures were taken by LumiCube (Liponics, Inc., 5003). After the pictures had been taken, the film was washed three times for 10 minutes with TBS-T and was dipped in a CBB dyeing liquid (PAGE Blue 83, COSMO BIO CO., LTD., 423406) for ten minutes, and bands of proteins were observed (FIG. 2).

Figure 2:
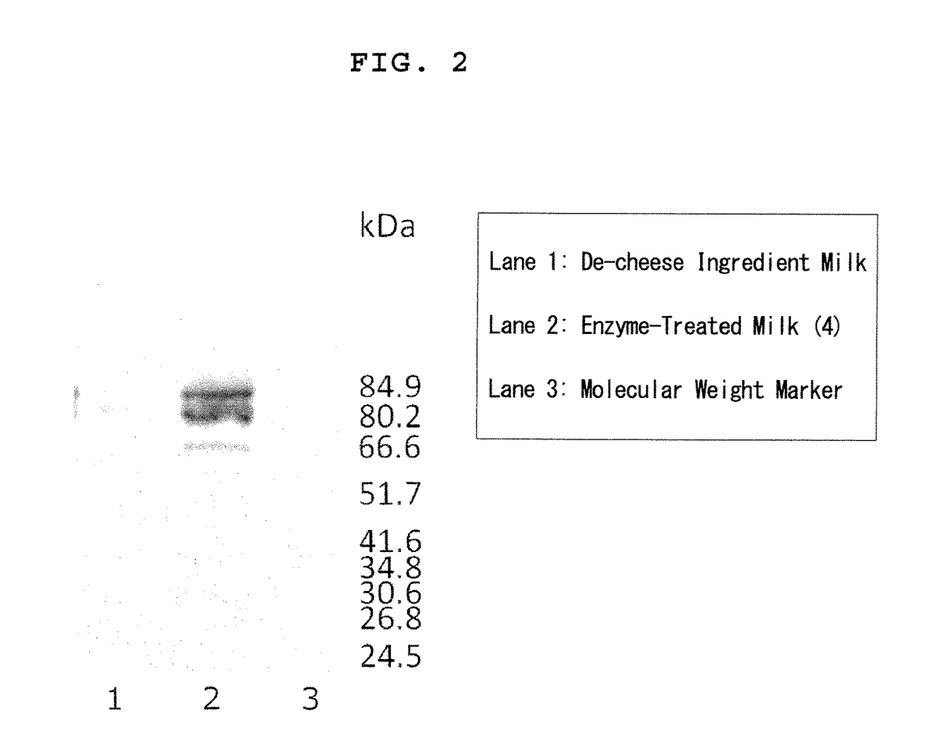
FIG. 2 is a photograph used in place of a drawing, which shows the results of electrophoresis of enzyme-treated milk product (4).

In FIG. 2, the molecular weight of WFA positive bands in the enzyme-treated milk (4) were identified with 24.5 kDa, 26.8 kDa, 30.6 kDa, 34.8 kDa, 41.5 kDa, 51.7 kDa, 66.6 kDa, 80.2 kDa, and 84.8 kDa, respectively.

The WAF as the primary antibody is the antibody recognizing GalNAc.

6. Western Blotting (2) for the Enzyme-Treated Milk (4) and the De-Cheese Ingredient Milk. (Using Anti-Vitamin D Binding-Protein Antibody as Primary Antibody)

Western blotting was performed in the same manner as described in the above "Western Blotting (1)" using anti-vitamin D binding-protein antibody [prepared from 10 μl of Anti-Vitamin D Binding protein Antibody (Bioss Co., bs-3915R) by diluting with 10 ml of TBS-T] as primary antibody, instead of WFA, and further using Anti-Rabbit IgG [prepared from 1 μl of Anti-Rabbit IgG (whole molecule) 1ML (SIGMA, A6154-1ML) by diluting with 10 ml of TBS-T], instead of streptavidin.

Figure 3:
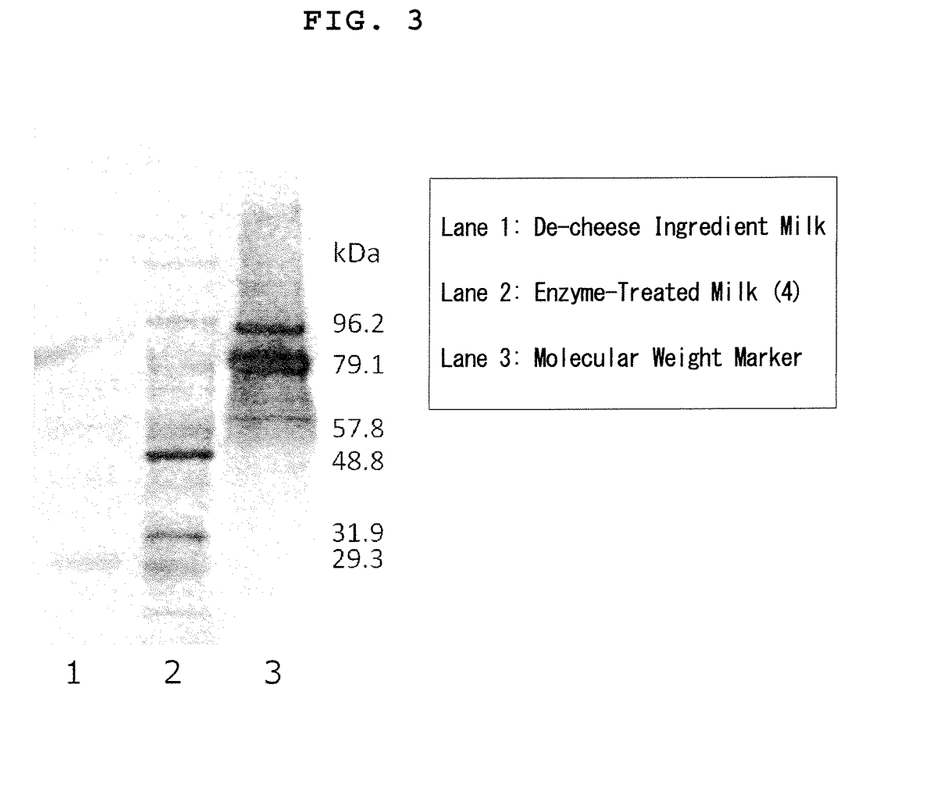
FIG. 3 is a photograph used in place of a drawing, which shows the results of electrophoresis of enzyme-treated milk product (4).

The results were shown in FIG. 3. In FIG. 3, the molecular weight of the positive bands in the enzyme-treated milk (4) were identified with 29.3 kDa, 31.9 kDa, 48.4 kDa, 57.8 kDa, 79.1 kDa, and 96.2 kDa, respectively.

The Anti-Vitamin D Binding protein Antibody as the primary antibody is the antibody recognizing the vitamin D binding protein.

INDUSTRIAL APPLICABILITY

According to the present invention, it is possible to provide an enzyme-treated milk product which is useful for treatment, prevention, and amelioration of diseases such as a cancer and an infectious disease, a disease associated with fatigue, allergic diseases (particularly caused by type I allergy), and an alopecia, as well as improvement of skin, and a method of preparing the same.

Further, the present invention provides a pharmaceutical compositions comprising the enzyme-treated milk product, pharmaceuticals and products comprising thereof.

EXPLANATION OF SYMBOLS

1: Phagocytosing macrophage
2: Phagocytosed SRBC
3: Macrophage

The invention claimed is:

1. A method of preparing an enzyme-treated milk product having macrophage activating action, the method comprising a step of
bringing a milk comprising milk proteins into contact with β-galactosidase and sialidase to increase an amount of a protein having GalNAc in the enzyme-treated milk product,
wherein one dose of said enzyme-treated milk product comprises a total protein concentration of 0.02 μg to 40 mg.

2. The preparation method according to claim 1, further comprising a step of condensation, or de-cheese processing of the milk, before enzyme treating.

3. An enzyme-treated milk product obtained by the preparation method according to claim 1.

4. A pharmaceutical composition comprising the enzyme-treated milk product according to claim 3.

5. A medicinal product comprising the pharmaceutical composition according to claim 4.

6. A composition for food or beverage comprising the enzyme-treated milk product according to claim 3.

7. A food or beverage comprising the composition for food or beverage according to claim 6.

8. An enzyme-treated milk product obtained by the preparation method according to claim 2.

9. The preparation method according to claim 1, wherein the β-galactosidase is soluble β-galactosidase.

* * * * *